United States Patent [19]
Klatz et al.

[11] Patent Number: 6,030,412
[45] Date of Patent: Feb. 29, 2000

[54] APPARATUS AND METHOD FOR COOLING THE BRAIN, BRAIN STEM AND ASSOCIATED NEUROLOGIC TISSUES

[75] Inventors: Ronald M. Klatz; Robert M. Goldman, both of Chicago, Ill.

[73] Assignee: Life Science Holdings, Inc., Chicago, Ill.

[21] Appl. No.: 08/901,164

[22] Filed: Jul. 28, 1997

Related U.S. Application Data

[63] Continuation-in-part of application No. 08/580,841, Dec. 29, 1995, and a continuation-in-part of application No. 08/447,812, May 23, 1995, which is a continuation of application No. 08/117,417, Sep. 7, 1993, abandoned, which is a continuation of application No. 07/704,038, May 22, 1991, Pat. No. 5,261,399.

[51] Int. Cl.[7] ....................................................... A61F 7/10
[52] U.S. Cl. ............................ 607/104; 607/109; 607/110
[58] Field of Search ............................... 607/96, 104, 107, 607/108, 109, 110, 111, 112; 165/46; 383/901; 128/898

[56] References Cited

U.S. PATENT DOCUMENTS

| | | |
|---|---|---|
| 2,521,780 | 9/1950 | Dodd . |
| 3,463,161 | 8/1969 | Andrassy . |
| 3,606,890 | 9/1971 | Gilbert . |
| 3,760,056 | 9/1973 | Rudy ........................................ 607/111 |
| 3,871,381 | 3/1975 | Roslonski . |
| 3,908,655 | 9/1975 | Lund . |

(List continued on next page.)

FOREIGN PATENT DOCUMENTS

| | | |
|---|---|---|
| 0 449 299 A1 | 10/1991 | European Pat. Off. . |
| 3039 468 A1 | 5/1982 | Germany . |
| 8607793 | 1/1987 | Germany . |
| 9000752 | 10/1991 | Netherlands . |
| 446907 | 11/1974 | U.S.S.R. . |
| 454907 | 7/1975 | U.S.S.R. . |
| 652942 | 3/1979 | U.S.S.R. . |
| 904695 | 2/1982 | U.S.S.R. . |
| 1138152 | 2/1983 | U.S.S.R. . |
| 1138152 | 2/1985 | U.S.S.R. . |
| 2130489 | 6/1984 | United Kingdom . |
| 82/04184 | 12/1982 | WIPO . |
| 89/09583 | 10/1989 | WIPO . |

OTHER PUBLICATIONS

Talan, Jamie, "Brain Research: A Chilling Effect", Newsday, Apr. 14, 1992, p. 6.

*Primary Examiner*—Linda C. M. Dvorak
*Assistant Examiner*—R. Kearney
*Attorney, Agent, or Firm*—Oliff & Berridge, PLC

[57] ABSTRACT

A portable apparatus and corresponding method is provided for treating or preventing at least one of brain, brain-stem and associated nervous tissue injuries in a mammal suffering from decreased blood flow to the brain. The apparatus includes a flexible enveloping member for enveloping a head, neck and upper back of a mammal. The enveloping member includes outer and inner shells with at least one cavity intermediate the outer and inner shells for holding a coolant fluid within the at least one cavity. A coolant source is provided in communication with the enveloping member. The coolant source is capable of instantaneously providing a coolant fluid chilled to a temperature sufficient to slow the metabolism of the brain, whereby when the coolant source is activated, the enveloping member becomes instantly chilled rapidly cooling the brain to a temperature sufficient to slow the metabolism of the brain a sufficient amount so that the mammal remains neurologically intact while efforts are made to restore regular blood flow to the brain of the mammal.

30 Claims, 9 Drawing Sheets

U.S. PATENT DOCUMENTS

| | | | |
|---|---|---|---|
| 4,138,743 | 2/1979 | Elkins et al. | |
| 4,382,446 | 5/1983 | Truelock et al. | |
| 4,552,149 | 11/1985 | Tatsuki | |
| 4,691,762 | 9/1987 | Elkins et al. | |
| 4,750,493 | 6/1988 | Brader | |
| 4,753,242 | 6/1988 | Saggers | |
| 4,765,338 | 8/1988 | Turner et al. | |
| 4,869,250 | 9/1989 | Bitterly | |
| 4,920,963 | 5/1990 | Brader | |
| 5,163,425 | 11/1992 | Nambu et al. | |
| 5,261,399 | 11/1993 | Klatz et al. | |
| 5,350,417 | 9/1994 | Augustine | |
| 5,383,918 | 1/1995 | Panetta | |
| 5,486,207 | 1/1996 | Mahawili | |
| 5,539,934 | 7/1996 | Ponder | |
| 5,658,324 | 8/1997 | Bailey, Sr. et al. | |
| 5,692,238 | 12/1997 | Watson, Jr. | 607/108 |
| 5,755,756 | 5/1998 | Freedman, Jr. et al. | |
| 5,792,213 | 8/1998 | Bowen | 607/96 |
| 5,871,526 | 2/1999 | Gibbs et al. | 607/114 |

APPARATUS AND METHOD FOR COOLING THE BRAIN, BRAIN STEM AND ASSOCIATED NEUROLOGIC TISSUES

This application is a continuation in part of U.S. patent application Ser. No. 08/580,841, filed on Dec. 29, 1995, and a continuation in part of U.S. patent application Ser. No. 08/447,812, filed May 23, 1995, which is in turn a continuation of U.S. patent application Ser. No. 08/117,417, filed Sep. 7, 1993, now abandoned, which is in turn a continuation of U.S. application patent Ser. No. 07/704,038, filed May 22, 1991, now U.S. Pat. No. 5,261,399.

BACKGROUND OF THE INVENTION

1. Field of Invention

The invention relates generally to cooling of the brain, brain stem and associated tissues during trauma, or periods of decreased blood flow to reduce or prevent neurologic injuries thereto due to ischemia and anoxia. More particularly, the invention provides an apparatus and corresponding method for cooling of the brain, brain stem and associated neurologic tissues and maintaining them at a temperature sufficient to slow metabolic rates of the brain, brain stem and associated tissues a sufficient amount to reduce or prevent neurologic injuries thereto due to ischemia and anoxia. With the invention, the victim recovers with increased chances of survival and less chance of permanent brain damage.

2. Description of Related Art

When an ischemic or anoxic injury occurs, the brain is deprived of freshly oxygenated blood. For example, this situation typically occurs during cardiac arrest, respiratory arrest, stroke and other cerebrovascular trauma, suffocation, drowning, strangulation, electrocution, toxic poisoning (carbon monoxide, cyanide, etc.), metabolic insults or other similar trauma. Without a steady supply of freshly oxygenated blood, the brain ceases to function and after resuscitation, most patients will suffer some damage to the brain and associated neurologic tissues.

For example, among cardiac arrest victims overall less than 10% survive neurologically intact and without significant brain damage. The other approximately 90% either die or sustain some neurologic injury from ischemia (i.e., lack of blood flow to the brain), or anoxia (i.e., lack of oxygen to the brain). Such frequency of neurologic injury occurs because after a cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving the brain in addition to resuscitating the heart.

As indicated above, anoxic and ischemic brain injuries from cardiac arrest result in damage to the brain and associated neurologic tissues after about four minutes. In contrast, the heart can survive intact up to four hours after cardiac arrest. The short viability of brain tissue upon deprivation of oxygenated blood is a result of the requirement of high amounts of nutrients for tissue maintenance. Brain tissue uses almost all of the nutrients supplied by the circulating blood for maintenance and stores only a small amount of nutrients. Absent blood flow to the brain, the small amount of stored nutrients is rapidly exhausted. Once exhausted, brain oxygen content is rapidly depleted. This oxygen depletion is traumatic and causes a series of reactions in the oxygen starved brain tissue cells. These reactions are believed to produce free radical ions, primarily consisting of the superoxide radical $O_2^-$. These free radicals complex with proteins in the brain and associated neurologic tissues, altering respiration, energy transfer and other vital cellular functions, and irreversibly damage these tissues.

Efforts should be directed toward resuscitating the brain to attempt to extend the period of time the brain can function without oxygen while the patient remains neurologically intact. The medical literature is replete with examples of humans surviving extended periods of time (greater than 5 minutes) without oxygen being delivered to the brain.

Hypothermic therapy is one method of keeping the brain alive absent oxygen. It involves cooling the brain to a temperature where its metabolic activity is decreased. When the brain's metabolic activity is decreased, it uses much less oxygen and stored nutrients are exhausted slowly, while production of irreversibly damaging $O_2^-$ free radicals is slowed and almost completely ceased. Thus, upon resuscitating the body from trauma, the patient emerges neurologically intact. For example, children revived after hours of submersion in very cold water have fully recovered with little if any neurologic damage.

Previous inventions, such as those described in U.S. Pat. No. 5,149,321 to Klatz et al. ('321), U.S. Pat. No. 5,234,405 to Klatz et al. ('405), U.S. Pat. No. 5,261,399 to Klatz et al. ('399) and co-pending U.S. Application Ser. No. 08/447,812 ('812), address the need to direct resuscitation efforts toward the brain, such that the victim can survive ischemic or anoxic trauma neurologically intact. Specifically, the '321 and '405 patents discuss devices and methods for resuscitating the brain such that its metabolism is slowed in order that the victim survive these metabolic insults neurologically intact. The '399 patent and the '812 application disclose a device and method for externally cooling the brain and associated tissues.

Russian Patents Nos. 1138152 ('152) and 904,695 ('695) disclose helmets for treatment of the head with cold or heat. However, the helmets of the '152 and '695 patents are not suited for field use, as they are large structures restricted to clinical facilities. Moreover, they must be used by a skilled surgical team and maintained by skilled technicians and are not disposable. Further, neither of these devices is configured to cool the neck and upper back.

Brain cooling devices, such as those disclosed in U.S. Pat. No. 4,920,963 and Russian Patents Nos. 652,942 ('942), 454,907 ('907) and 446,015 ('015), are complex and require that the patient be placed into the device lying down. The '907 patent discloses using chilled water to effectuate cooling and the '942 and '015 patents are silent as to whether they have the capability of chilling the brain, brain stem and associated neurologic tissues a sufficient amount to reduce or prevent ischemic and anoxic injuries thereto. Further, none of these devices are disposable or suitable for field use due to their structure. Nor are any of these devices configured to cool the neck and upper back.

Various other patent documents disclose apparatus for cooling the head, for example, International Patent Publication No. WO 82/04184 ('184), International Patent Publication No. WO 89/09583 ('583), U.S. Pat. No. 4,753,242 ('242), British Patent No. 2,130,489 ('489), German Patent No. 8607793 ('793), and U.S. Pat. Nos. 3,909,655 ('655), 3,606,890 ('890), 4,691,762 ('762) and 4,138,743 ('743). These devices cool the head respectively to treat chemotherapy patients suffering from alopecia (hair loss); to treat post-operative plastic surgery patients; to treat patients suffering from migraines; or merely to provide a beauty treatment or for personal comfort. However, these devices are not capable of providing the cooling sufficient to slow metabolic rates of the brain, brain stem and associated tissues a sufficient amount to reduce or prevent neurologic injuries thereto due to ischemia and anoxia. Further, these devices are generally complicated, designed for clinical use, not disposable and are not configured to cool the neck and upper back.

SUMMARY OF THE INVENTION

It is therefore an object of the invention to non-invasively and inexpensively treat ischemic and anoxic injuries promptly upon cardiac arrest. Resuscitation efforts are applied in time for a patient to survive neurologically intact. By directing resuscitation efforts to treat the brain promptly, the invention allows emergency personnel substantial additional time (beyond the critical four minute window) to regain the failed heart's circulation without the patient suffering permanent neurologic damage.

It is a further object of this invention to provide a method for treating anoxic or ischemic injuries to the brain whereby the patient survives neurologically intact.

It is also an object of the invention to provide a method of treating ischemic and anoxic brain injuries so as to inhibit free radical chemical species from complexing with proteins in the brain and neurologic tissue to avoid permanent irreversible damage.

It is a further object of the invention to provide an apparatus which can substantially instantaneously cool the brain, brain stem and associated tissues to a temperature sufficient to slow the metabolic rates a sufficient amount to reduce or prevent neurologic damage due to anoxia and ischemia.

It is a further object of the invention to provide a portable apparatus for non-invasively treating anoxic and ischemic brain injuries which can substantially instantaneously cool the brain and associated neurologic tissue.

It is yet anther object of the invention to provide an apparatus for treating the aforementioned injuries by instantaneously cooling the brain, brain stem, and associated neurologic tissues and the upper spinal column.

It is further an object of the invention to provide an apparatus for treating the aforementioned injuries, which is suited for field, as well as clinical, use and that can be operated by a single person with minimal medical training and experience.

It is a still further object to provide apparatus for cooling the brain which has very few parts, is economical to manufacture, easy to use and disposable.

Accordingly, the invention includes a non-invasive method for treating or preventing at least one of brain, brain stem and associated nervous tissue injuries in a mammal suffering from decreased blood flow to the brain. The method includes placing over the head, and optionally also the neck and lower back, of a mammal (e.g., patient) a flexible enveloping member. The enveloping member includes outer and inner shells with at least one cavity intermediate the outer and inner shells for holding a coolant fluid within the at least one cavity. A coolant source in communication with the enveloping means provides a coolant fluid instantaneously chilled upon activation to a temperature sufficient to slow the metabolism of the brain of the mammal a sufficient amount so that the mammal remains neurologically intact while efforts are made to restore regular blood flow to the brain of the mammal.

The invention further provides an apparatus for treating or preventing at least one of brain, brain-stem and associated nervous tissue injuries in a mammal suffering from decreased blood flow to the brain. The apparatus includes a flexible enveloping member for enveloping a head, and optionally also a neck and upper back, of a mammal. The enveloping member includes outer and inner shells with at least one cavity intermediate the outer and inner shells for holding a coolant fluid within the at least one cavity. A coolant source is provided in communication with the enveloping member. The coolant source is capable of instantaneously providing a coolant fluid chilled to a temperature sufficient to slow the metabolism of the brain. When the coolant source is activated, the enveloping member becomes instantly chilled, rapidly cooling the brain to a temperature sufficient to slow the metabolism of the brain a sufficient amount so that the mammal remains neurologically intact while efforts are made to restore regular blood flow to the brain of the mammal.

The enveloping member may, for example, be in the shape of a scarf, or alternatively, in the shape of a poncho.

Further, the coolant source may be a portable coolant tank containing compressed liquid, the portable coolant tank being in fluid communication with the at least one cavity of the enveloping means via a tube. As other alternatives, the coolant source may be a portable coolant refrigeration unit in fluid communication with the at least one cavity of the enveloping means via inlet and outlet tubes, which provide for two-way or recirculating flow of coolant fluid between the coolant source and the at least one cavity; may include a packet containing chemicals which are activated upon mixing to produce the chilled coolant fluid; may be a charging mechanism disposed on an outer surface of the outer shell which upon activation produces the chilled coolant fluid; or may be a chemical disposed within the at least one cavity which produces the chilled coolant fluid when activated by another chemical.

Also, the enveloping member may be configured and formed of appropriate materials to be disposable. Further, a flexible adjusting mechanism may be provided for maintaining the enveloping member on the head of a mammal. A layer of gel may be disposed on an inner surface of the inner shell. Additionally, the enveloping member may include a removable or hinged flap for cooling at least a portion of the face of a mammal.

Additionally, the apparatus according to the invention may include a hard outer shell configured to house the flexible enveloping member. The hard outer shell may include a head enveloping portion, a flexible neck enveloping portion and an upper back enveloping portion, which correspond to the head, neck and upper back enveloping portions of the flexible enveloping member. The flexible enveloping member may be affixed to the hard outer shell via, for example, hook and loop fasteners (e.g., Velcro®), hooks, snaps, buttons, or adhesive.

The cooling apparatus may also include at least one inflatable bladder in communication with an inflation device such that the at least one inflatable bladder is inflated by the inflation device to press the enveloping means against the head, neck and upper back of a mammal, whereby the head, neck and upper back of the mammal are rapidly cooled.

BRIEF DESCRIPTION OF THE DRAWINGS

These and other aspects and advantages of the invention will become apparent from the following detailed description of preferred embodiments when taken in conjunction with the accompanying drawings, in which.

DETAILED DESCRIPTION OF PREFERRED EMBODIMENTS

While the invention will hereinafter be described in connection with preferred embodiments thereof, it will be understood that it is not intended to limit the invention to those embodiments. On the contrary, it is intended to cover all alternatives, modifications and equivalents that may be included within the spirit and scope of the invention as defined by the appended claims.

For a general understanding of the features of the invention, reference is made to the drawings. In the drawings, like reference numerals have been used throughout to designate like elements.

Figure 1:
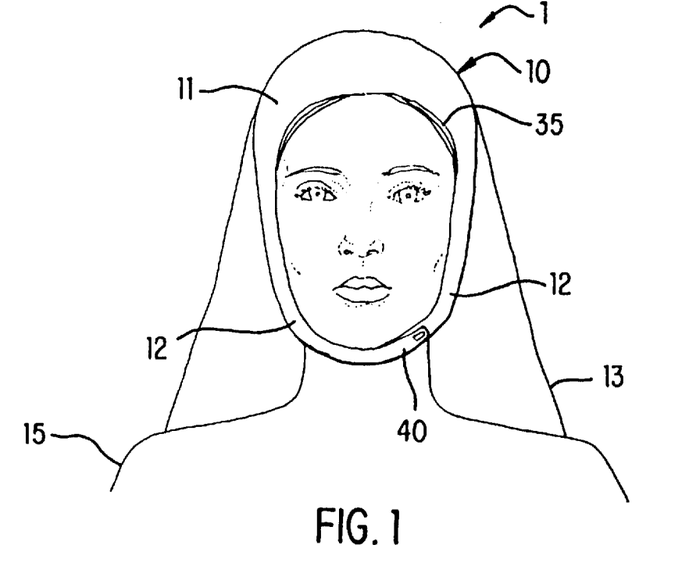
FIG. 1 is a front view of an embodiment of a cooling apparatus according to the invention.
Figure 2:
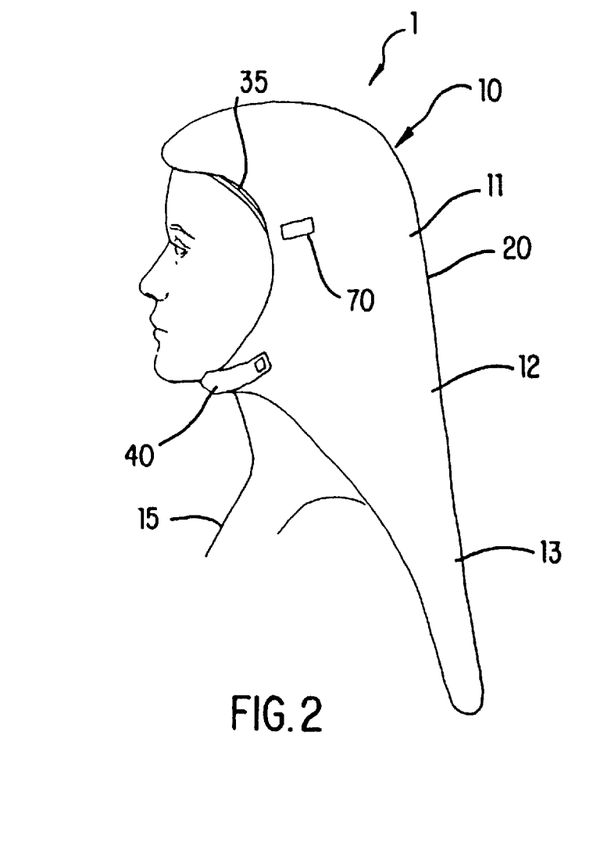
FIG. 2 is a side view of the cooling apparatus of FIG. 1.
Figure 6:
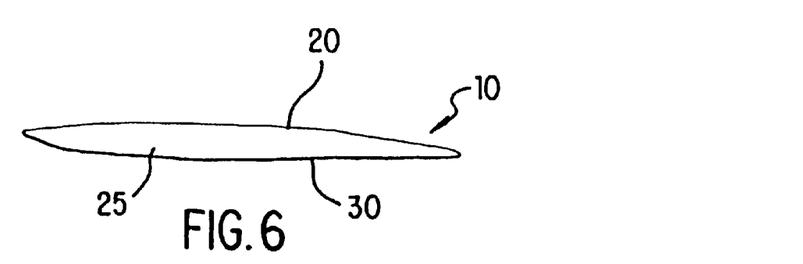
FIG. 6 is a cross-sectional view of the cooling apparatus of FIG. 1 taken along line IV—IV of FIG. 3.

FIG. 1 is a front view of a preferred embodiment of the cooling apparatus according to the invention, while FIG. 2 is a side view of the cooling apparatus of FIG. 1. The cooling apparatus 1 shown in FIG. 1 is preferably formed of a scarf-shaped enveloping member 10. The enveloping member 10 is formed by outer 20 and inner 30 shell members, which are sealed together along their outer peripheral edges to form a cavity 25 (see FIG. 6). The enveloping member 10 preferably includes a head-enveloping portion 11, a neck enveloping portion 12 and an upper back-enveloping portion 13, preferably connected in series.

The outer shell member 20 and the inner shell member 30 are preferably made of a flexible, inexpensive material so that the enveloping member 10 may be used once and then discarded. The material may also include such materials as TEFLON®, TYVEC®, Gore-tex®, nylon, rubber or any non-porous flexible material.

Figure 3:
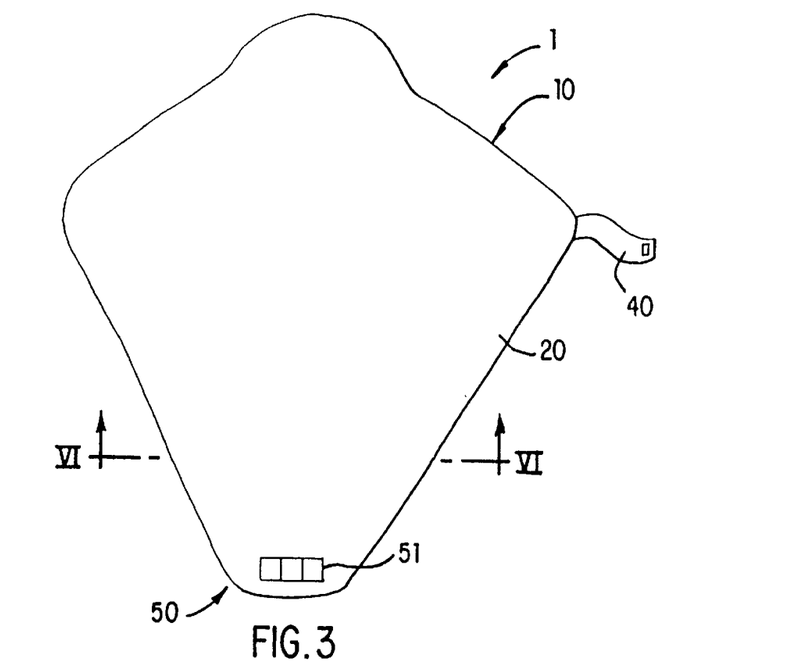
FIG. 3 is a top plan view of the cooling apparatus of FIG. 1.

A coolant source 50 is configured to supply the cavity 25 with coolant fluid chilled to a temperature sufficient to slow the metabolic rates of the brain, brain stem and associated tissues of a patient 15 a sufficient amount to reduce or prevent neurologic injuries thereto due to ischemia and anoxia. The coolant source 50 can be in the form of a charging mechanism 51 disposed on an outer surface of the outer shell member 20, as shown in FIG. 3. Such a charging mechanism 51 could contain compressed gas that would expand into the cavity 25 upon activation to provide the chilled coolant fluid.

Figure 4:
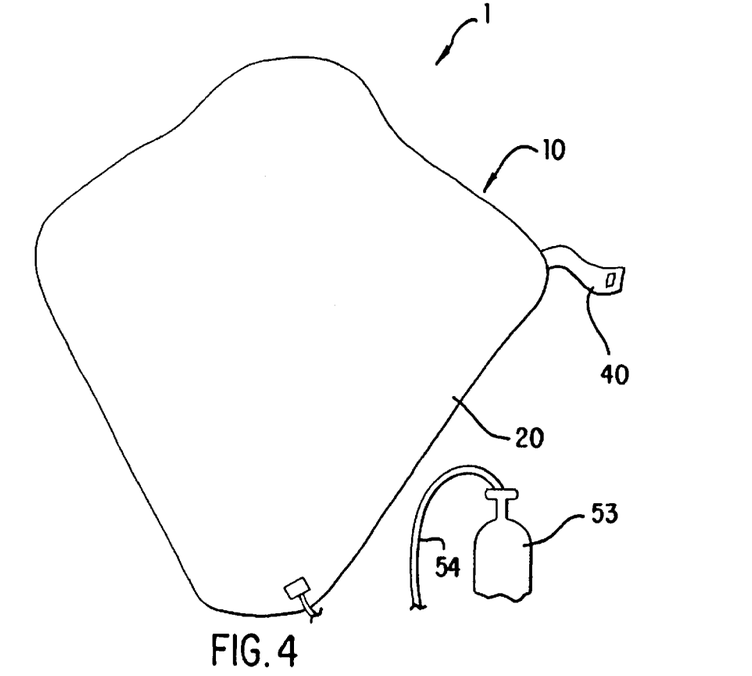
FIG. 4 is a top plan view of the cooling apparatus of FIG. 1 employing an alternative coolant source.
Figure 4A:
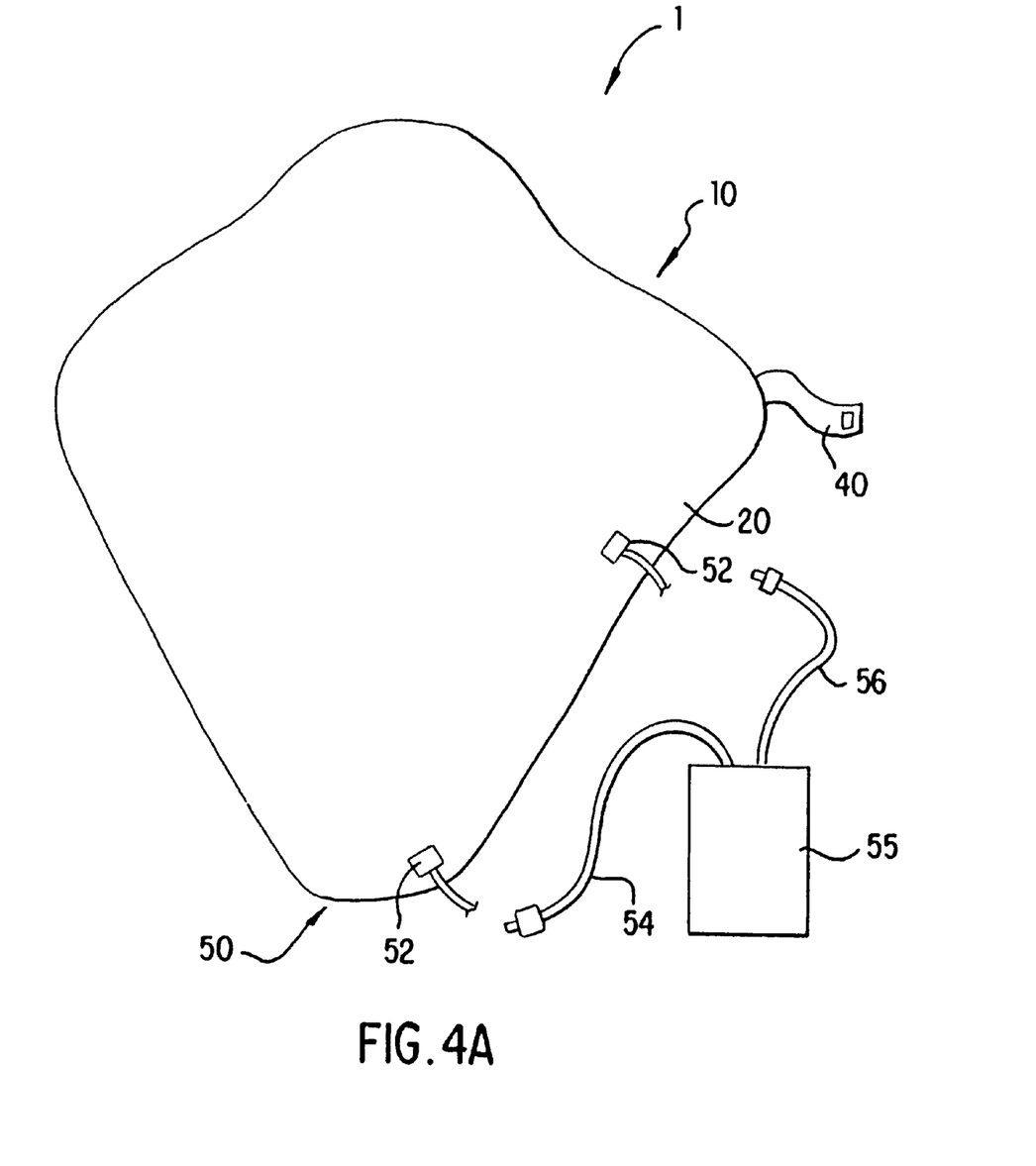
FIG. 4A is a top plan view of the cooling apparatus of FIG. 1 employing another alternative coolant source.
Figure 5:
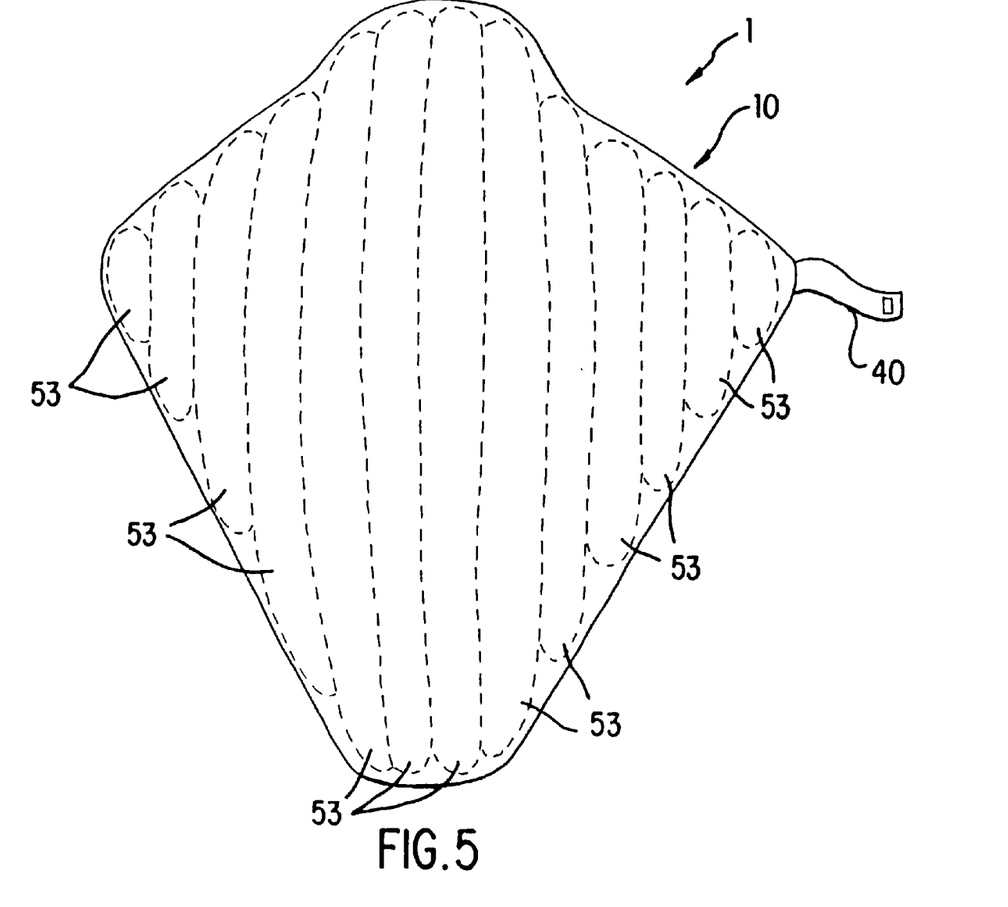
FIG. 5 is a top plan view of the cooling apparatus of FIG. 1 employing another alternative coolant source.

Alternatively, the coolant source 50 may comprise cold compressed liquids, such as, for example, carbon dioxide, freon or nitrogen, which upon decompression become cold gases, preferably stored in a portable container 53, such as, for example, a cartridge or tank (see FIG. 4). The gas preferably turns to dry ice upon expansion. The cavity 25 could also contain materials which chill upon activation when use is desired. For example, the cavity could be prefilled with a chemical, such as ammonium nitrate or an equivalent thereof, which reacts endothermically when activated by another chemical (e.g., water), chilling the device, or may contain materials activatable when exposed to a catalyst or enzyme activator. Alternatively, very cold liquids such as supercooled water, self freezing gel, packed liquid, ice water, or other such chemicals may be passed into the apparatus 10 through a tube 54 operatively connected to the nipple 52, or chilled by a refrigeration unit 55 which provides for two-way flow or circulation of the chilled fluid though the enveloping member 10 (see FIG. 4A). The refrigeration unit 55 could be computer controlled via a microprocessor in communication with a temperature sensor or sensors (not shown) which monitors the temperature in the enveloping member 10. The coolant source 50 may also be chemical packets 53 disposed within the cavity 25, which are activated when a membrane dividing the cavity into two or more chemical containing compartments is broken to allow the chemicals to mix (see FIG. 5), or which contain an ice-like material, such as blue ice, which is chilled in a refrigeration unit (not shown) until the apparatus is put to use. Additionally, the enveloping member 10 could include a quick charge valve acting as a coolant source to allow the device (not shown) to be rapidly filled with a coolant fluid, such as common crushed ice or snow.

In the case where the coolant source 50 is the charging mechanism, or the portable container 53, the outer shell member 20 may be provided with exhaust ports (not shown) to allow exit of the coolant fluid from the enveloping member 10. Further, the enveloping member 10 may be provided with means for collecting the exhausted coolant fluid for later disposal. Preferred coolant sources 29 are capable of generating temperatures as low as −60 degrees Fahrenheit, and preferably temperatures approximately −10 degrees Fahrenheit or below.

FIGS. 1–5 show a flexible closure device 40. The flexible closure device 40 should be elastic enough to allow for adjustment to various head sizes, yet resilient enough to maintain the enveloping member 10 on the head of the patient 15. The closure device 40 is preferably formed of quick release structure such as VELCRO®, or other suitable fastening materials. Mechanisms such as zippers, combinations of VELCRO® and zippers, or other equivalent fasteners can also be used to make this connection.

Further, the head enveloping portion 11 may be provided with a tightening mechanism 35, such as a draw string or elastic, for tightening the head enveloping portion 11 around the exposed face of the patient 15.

The inner layer of the inner shell member 30 may be coated with gel, such as any commercially available EKG electrode gel or ultrasound gel. The gel would be retained under paper, wax-based or TYVEK® type sheets, that peel off when use of the apparatus is desired.

As discussed above, a temperature sensor or sensors (not shown) and a microprocessor (not shown) may be used to allow control of the refrigeration unit 55, which would maintain the temperature within the enveloping member 10 by controlling a valve (not shown) to provide fresh chilled coolant fluid when needed. Further, the enveloping member 10 may be provided with a temperature display 70 to allow one to assess the temperature at which the cooling apparatus 1 is performing.

Figure 7:
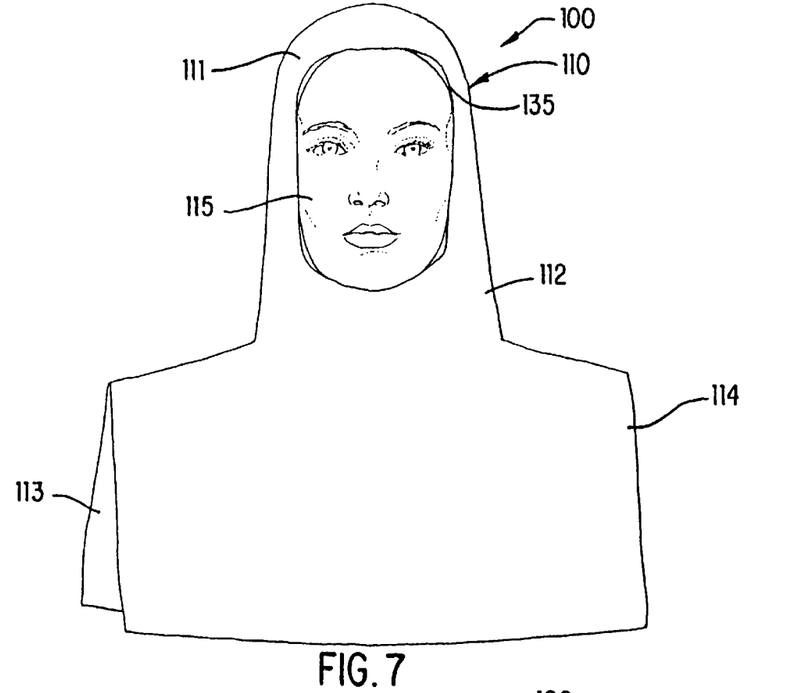
FIG. 7 is a front view of another embodiment of the cooling apparatus according to the invention.
Figure 8:
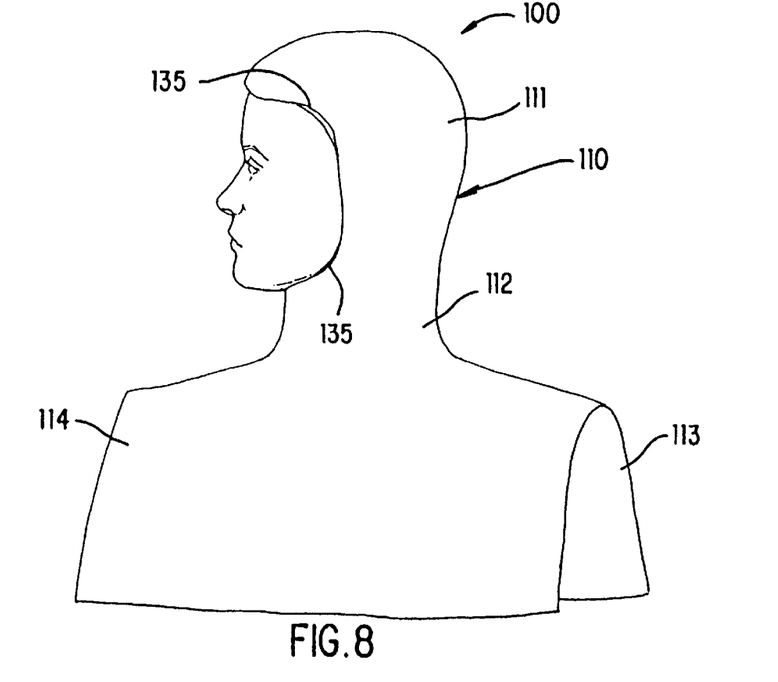
FIG. 8 is a side view of the cooling apparatus of FIG. 7.

FIGS. 7 and 8 disclose another embodiment of the cooling apparatus according to the invention. The cooling apparatus 100 of FIGS. 7 and 8 is in the style of a poncho-shaped enveloping member 110. In addition to having a head-enveloping portion 111, a neck enveloping portion 112 and an upper back-enveloping portion 113, this embodiment has a chest-enveloping portion 114. Otherwise, this embodiment may be structured the same as the embodiment of FIGS. 1–6, and will not be further discussed in detail.

Figure 9:
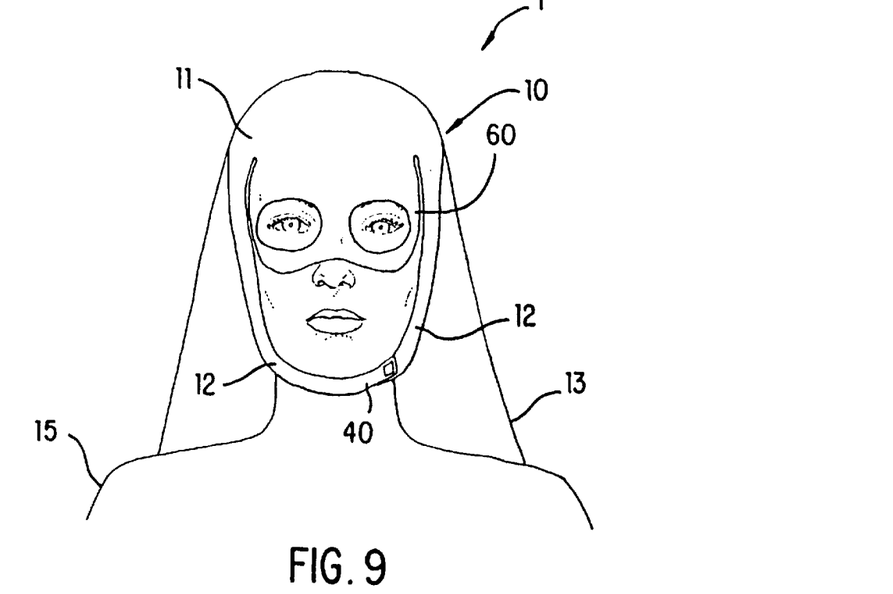
FIG. 9 shows the cooling apparatus of FIG. 1 with an eye flap.

FIG. 9 shows an embodiment similar to that of FIGS. 1–6 with a removable or hinged flap 60 for cooling the forehead of the patient 15. The flap may be extended down to cover the nose, cheeks, and/or chin of the patient to provide additional cooling, as long as it is provided with openings to accommodate the patient's mouth and nostrils. The flap may be transparent to allow emergency personnel to monitor any facial wounds. Any of the embodiments discussed in this application can include the flap 60 or the like.

Figure 10:
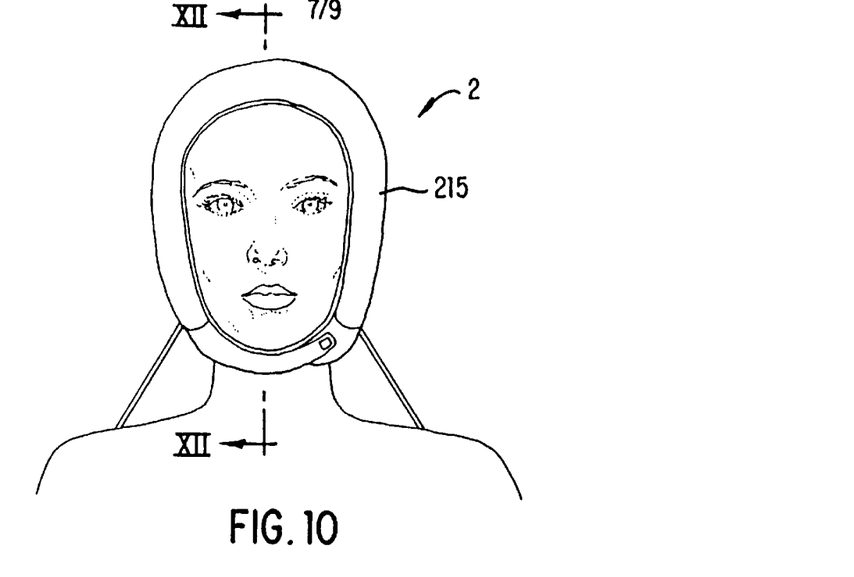
FIG. 10 is a front view of still another embodiment of the cooling apparatus according to the invention.
Figure 11:
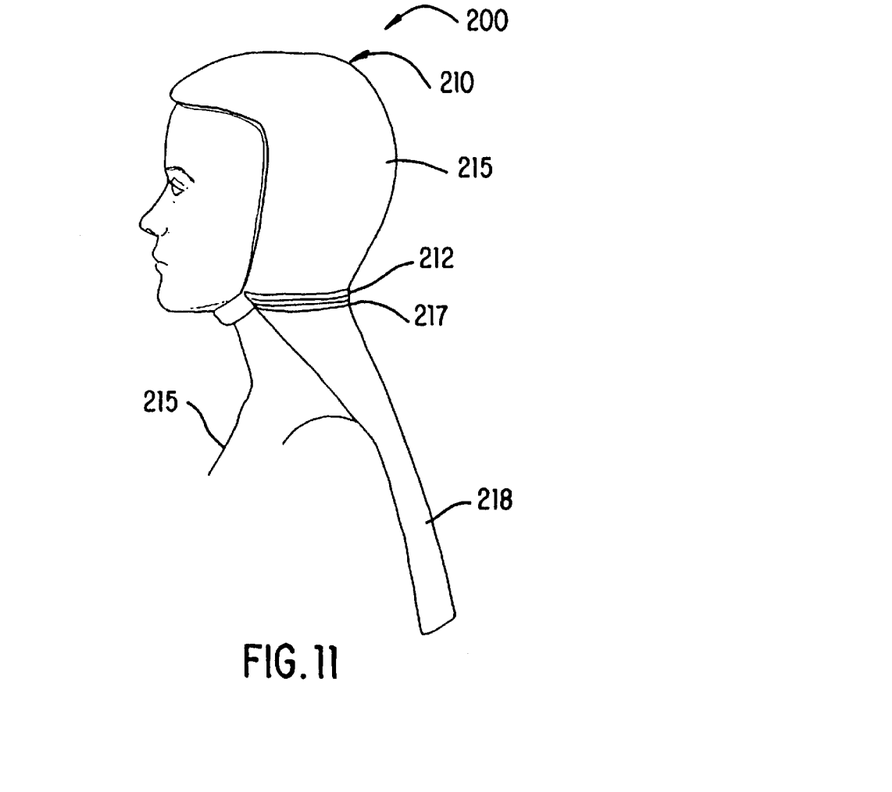
FIG. 11 is a side view of the cooling apparatus of FIG. 10.
Figure 12:
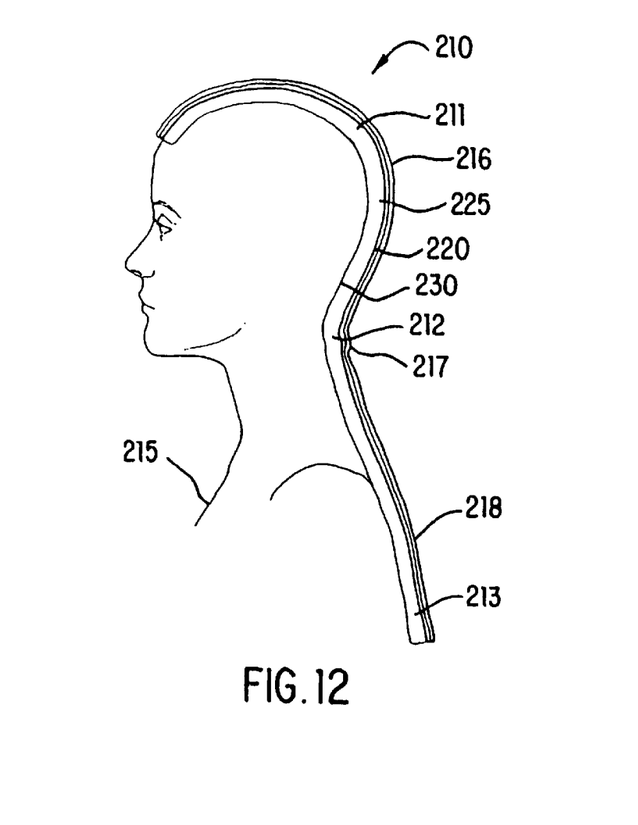
FIG. 12 is a cross-sectional view of the cooling apparatus of FIG. 10 taken along line XII—XII of FIG. 10.

FIGS. 10–12 show yet another embodiment of the invention. In this embodiment, the cooling apparatus is structured similar to that of FIGS. 1–6. However, the cooling apparatus 200 is further provided with a hard outer shell in which the flexible enveloping member 210 is securely fastened by means of, for example, hooks, Velcro®, or adhesive. The hard outer shell includes a head-enveloping portion 216, a flexible neck-enveloping portion 217 and an upper back-enveloping portion 218, which correspond respectively to the head-enveloping portion 211, the neck-enveloping portion 212 and upper back-enveloping portion 213 of the flexible enveloping member 210. Where the enveloping member 210 is configured to be disposable, the hard outer shell preferably is configured to be used over and over again with different enveloping members.

Figure 13:
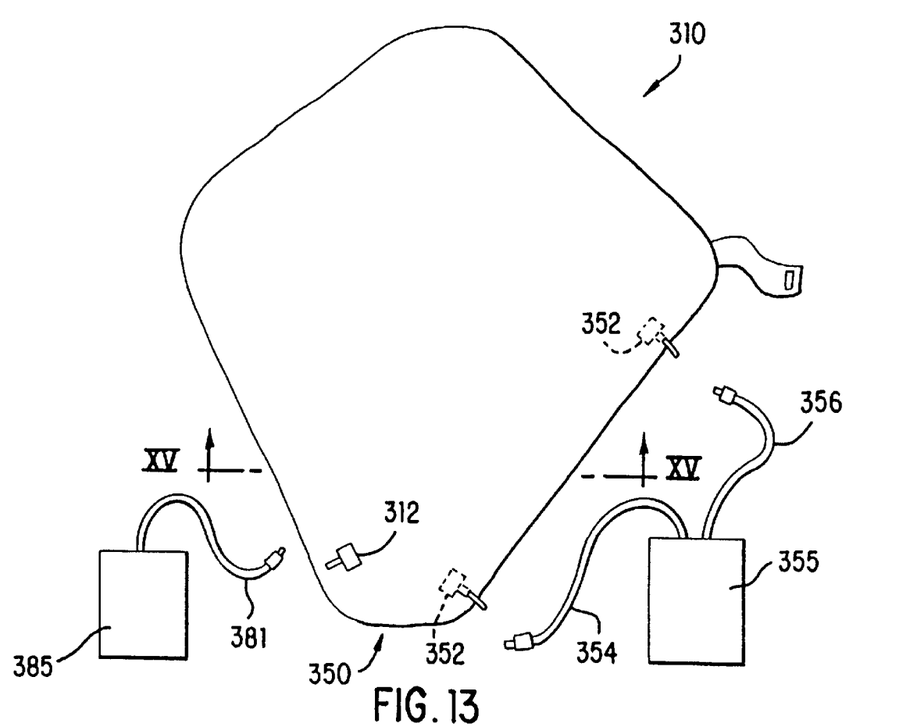
FIG. 13 is a front view of yet another embodiment of the cooling apparatus according to the invention.
Figure 14:
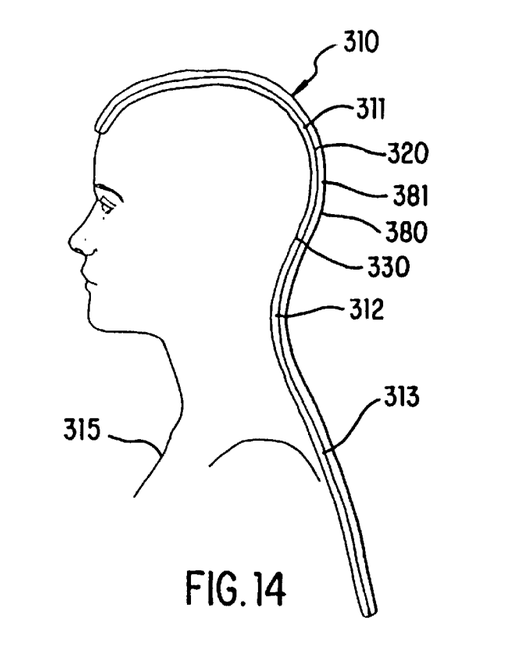
FIG. 14 is a side cross-sectional view of the cooling apparatus of FIG. 12.
Figure 15:
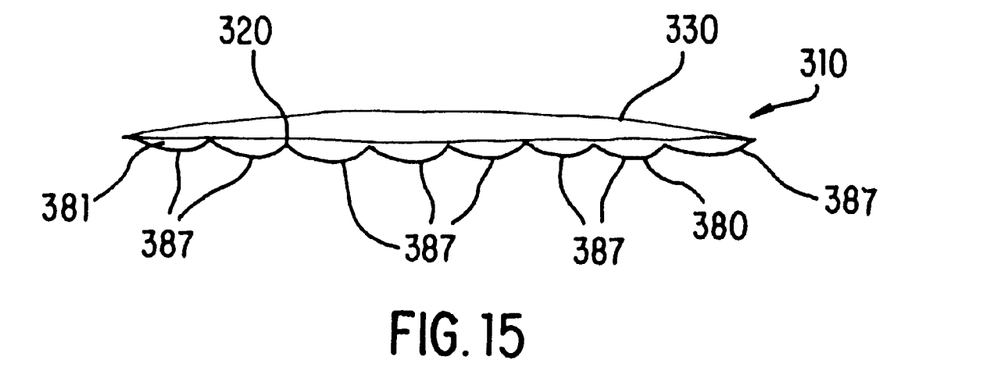
FIG. 15 is a cross-sectional view of the cooling apparatus of FIG. 13 taken along line XV—XV of FIG. 13.

FIGS. 13–15 show still another embodiment of the invention. In this embodiment, the enveloping member 310 of the cooling apparatus 300 is provided with a bladder layer 380 in addition to the outer and inner shell members 320, 330. The bladder layer 380 is sealed together to the outer and inner shell members 320, 330 to form an air bladder, or cavity 381 with the outer shell member 330. The bladder layer 380 is provided with a nipple 382 to which a gas source 385 may be attached via a tube 384 to fill the cavity 381 with a gas (i.e., air, nitrogen, helium, oxygen, or carbon dioxide) to press the outer and inner shell members 320, 330 against the head, neck and upper back of the patient 315 to provide greater contact therebetween. This contact facilitates heat transfer between the cooling apparatus 310 and the head, neck and upper back of the patient 315, and therefore provides for more rapid body cooling. Alternatively, an air bladder or bladders can be configured as a separate piece or pieces disposed on the outer shell member 330. As shown in FIG. 15, the cavity 381 can be provided with lumens 387 which cause the gas to circulate through the cavity 381 for even distribution. These lumens 387 are formed by heat sealing the bladder layer 380 to the outer shell member 330 at various places to define gas circulation paths.

In operation, the cooling apparatus of the invention sufficiently chills the brain, brain stem and associated neurologic tissues to slow their metabolism, allowing for continued resuscitation efforts. As previously stated, the invention comprises a method of treating anoxic and ischemic injuries suffered as a result of cardiac arrest, respiratory arrest, stroke or other cerebrovascular trauma, suffocation, drowning, electrocution, toxic poisoning (carbon monoxide, cyanide, etc.) metabolic insults or other similar trauma.

The operation of the cooling device according to the invention will now be discussed in detail with reference to the embodiment of FIGS. 1–6; however, the remaining embodiments in this application operate similarly. Specifically, operation of the cooling apparatus 1 involves merely placing the enveloping member 10 on the patient 15 such that it envelopes the head and neck and extends down to cover the upper back of the patient 15, and securing the neck-enveloping portion 12 around the neck of the patient 15 via the closure mechanism 40. Next, the coolant source 50 is connected to the enveloping member 10 if applicable (for example, attaching the tube 54 to the nipple 52). Then, the coolant source 50 is activated. In the case of the coolant packets 53, the coolant source 50 is activated by manual manipulation of the enveloping member 10 to break the compartment separating membrane. This process is quite simple and can be performed at the trauma site by a person with minimal, if any, medical training.

Each of these embodiments of the apparatus is portable and suitable for field use, such as in ambulances, battlefields, athletic fields, aircraft, marine vehicles, spacecraft, emergency treatment facilities, and the like. They are lightweight and can be carried directly to the patient. These embodiments can also be modified for clinical (hospital type) settings. While the apparatus of the invention is preferably designed for the treatment of humans, it can also be used in treating other mammals such as dogs, horses or the like, and sized accordingly.

While the invention has been described in conjunction with specific embodiments thereof, it is evident that many alternatives, modifications and variations may be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A portable apparatus for treating or preventing at least one of brain, brain-stem and associated nervous tissue injuries in a mammal suffering from decreased blood flow to the brain, comprising:

a flexible enveloping means for enveloping a head, neck and upper back of a mammal, the enveloping means including outer and inner shells with at least one cavity intermediate the outer and inner shells for holding a coolant fluid within the at least one cavity;

a coolant source in communication with the enveloping means, the coolant source instantaneously providing a coolant fluid chilled to a temperature sufficient to slow the metabolism of the brain, whereby when the coolant source is activated, the enveloping means becomes instantly chilled rapidly cooling the brain to a temperature sufficient to slow the metabolism of the brain a sufficient amount so that the mammal remains neurologically intact while efforts are made to restore regular blood flow to the brain of the mammal.

2. The apparatus according to claim 1, wherein the enveloping means is in the shape of a scarf which is configured to drape around the head, neck and upper back of a mammal to substantially encompass the head, neck and upper back of the mammal.

3. The apparatus according to claim 1, wherein the enveloping means is in the shape of a poncho.

4. The apparatus according to claim 1, wherein the coolant source is disposed within the at least one cavity and comprises a packet containing chemicals which are activated upon mixing to produce the chilled coolant fluid.

5. The apparatus according to claim 1, wherein the coolant source comprises a charging mechanism disposed on an outer surface of the outer shell which upon activation produces the chilled coolant fluid.

6. The apparatus according to claim 1, wherein the coolant source comprises a portable coolant tank containing compressed liquid, the portable coolant tank being in fluid communication with the at least one cavity of the enveloping means via a tube.

7. The apparatus according to claim 6, wherein the compressed liquid is selected from the group consisting of carbon dioxide, freon and nitrogen.

8. The apparatus according to claim 1, wherein the coolant source comprises a chemical disposed within the at least one cavity which produces the chilled coolant fluid when activated by another chemical.

9. The apparatus according to claim 8, wherein the chemical comprises ammonium nitrate which produces the chilled coolant fluid when activated by water.

10. The apparatus according to claim 1, further comprising flexible adjusting means for maintaining the enveloping means on the head of a mammal.

11. The apparatus according to claim 1, further comprising at least one temperature sensor in communication with the enveloping means that senses a temperature of the chilled coolant fluid within the enveloping means, and means for displaying the sensed temperature disposed on the outer shell.

12. The apparatus according to claim 11, wherein the at least one temperature sensor comprises a thermistor.

13. The apparatus according to claim 1, further comprising a removable or hinged flap for cooling at least a portion of the face of a mammal.

14. The apparatus according to claim 1, further comprising a hard outer shell configured to house the flexible enveloping means.

15. The apparatus according to claim 14, wherein the hard outer shell includes a head enveloping portion, a flexible neck enveloping portion and a upper back enveloping portion, which correspond to head, neck and upper back enveloping portions of the flexible enveloping means.

16. The apparatus according to claim 14, wherein the flexible enveloping means is affixed to the hard outer shell via at least one of hook-and-loop fasteners, hooks and adhesive.

17. The apparatus according to claim 1, further comprises means for pressing the enveloping means against the head, neck and upper back of a mammal, whereby the head, neck and upper back of the mammal are rapidly cooled.

18. The apparatus according to claim 1, wherein the enveloping means further comprises:

at least one inflatable bladder; and an inflation device in communication with the at least one inflatable bladder, wherein the at least one inflatable bladder is inflated by the inflation device to press the enveloping means against the head, neck and upper back of a mammal.

19. Apparatus for treating or preventing at least one of brain, brain stem and associated nervous tissue injuries in a mammal suffering from decreased blood flow to the brain, comprising:

flexible enveloping means for enveloping the head, neck and lower back of a mammal, the enveloping means including outer and inner shells with at least one cavity intermediate the outer and inner shells for holding a coolant fluid within the at least one cavity;

means for lowering the metabolism of the brain, brain stem and associated tissues of the mammal in communication with the enveloping means and comprising a coolant source that provides a coolant fluid instantaneously chilled upon activation to a temperature sufficient to slow the metabolism of the brain of the mammal a sufficient amount so that the mammal remains neurologically intact while efforts are made to restore regular blood flow to the brain of the mammal.

20. A method for treating or preventing at least one of brain, brain stem and associated nervous tissue injuries in a mammal suffering from decreased blood flow to the brain, comprising:

placing over the head, neck and lower back of a mammal a flexible enveloping means, the enveloping means including outer and inner shells with at least one cavity intermediate the outer and inner shells for holding a coolant fluid within the at least one cavity;

lowering the metabolism of the brain, brain step and associated tissues of the mammal by activating a coolant source in communication with the enveloping means, the coolant source providing a coolant fluid instantaneously chilled upon activation to a temperature sufficient to slow the metabolism of the brain of the mammal a sufficient amount so that the mammal remains neurologically intact while efforts are made to restore regular blood flow to the brain of the mammal.

21. The method according to claim 20, wherein the enveloping means is in the shape of a scarf.

22. The method according to claim 20, wherein the enveloping means is in the shape of a poncho.

23. The method according to claim 20, wherein the coolant source is disposed within the at least one cavity and comprises a packet containing chemicals which are activated upon mixing to produce the chilled coolant fluid.

24. The method according to claim 20, wherein the coolant source comprises a charging mechanism disposed on an outer surface of the outer shell which upon activation produces the chilled coolant fluid.

25. The method according to claim 20, wherein the coolant source comprises a portable coolant tank containing compressed liquid, the portable coolant tank being in fluid communication with the at least one cavity of the enveloping means via a tube.

26. The method according to claim 25, wherein the compressed liquid is selected from the group consisting of carbon dioxide, freon and nitrogen.

27. The method according to claim 20, wherein the coolant source comprises a portable coolant refrigeration unit in fluid communication with the at least one cavity of the enveloping means via inlet and outlet tubes.

28. The method according to claim 20, wherein the coolant source comprises a chemical disposed within the at least one cavity which produces the chilled coolant fluid when activated by another chemical.

29. The method according to claim 28, wherein the chemical comprises ammonium nitrate which produces the chilled coolant fluid when activated by water.

30. The method according to claim 20, wherein the enveloping means is configured to be disposable.

* * * * *